United States Patent
Arenson et al.

(10) Patent No.: US 7,149,278 B2
(45) Date of Patent: Dec. 12, 2006

(54) METHOD AND SYSTEM OF DYNAMICALLY CONTROLLING SHAPING TIME OF A PHOTON COUNTING ENERGY-SENSITIVE RADIATION DETECTOR TO ACCOMMODATE VARIATIONS IN INCIDENT RADIATION FLUX LEVELS

(75) Inventors: Jerome Arenson, Haifa (IL); David M. Hoffman, New Berlin, WI (US)

(73) Assignee: General Electric Company, Schenectady, NY (US)

( * ) Notice: Subject to any disclaimer, the term of this patent is extended or adjusted under 35 U.S.C. 154(b) by 77 days.

(21) Appl. No.: 10/711,329

(22) Filed: Sep. 10, 2004

(65) Prior Publication Data

US 2006/0056576 A1 Mar. 16, 2006

(51) Int. Cl.
*H05G 1/26* (2006.01)
(52) U.S. Cl. ............................................. 378/19; 378/5
(58) Field of Classification Search ................... 378/19, 378/5, 116; 250/370.09
See application file for complete search history.

(56) References Cited

U.S. PATENT DOCUMENTS

| 5,165,100 A | 11/1992 | Hsieh et al. |
| 5,400,378 A | 3/1995 | Toth |
| 5,416,815 A * | 5/1995 | Hsieh ............................. 378/4 |
| 2002/0001365 A1* | 1/2002 | Mazor et al. .................. 378/89 |

* cited by examiner

*Primary Examiner*—Edward J. Glick
*Assistant Examiner*—Hoon Song
(74) *Attorney, Agent, or Firm*—Ziolkowski Patent Solutions Group, SC; Michael A. Della Penna; Carl B. Horton

(57) ABSTRACT

A method and system of counting and tagging radiation energy received by a radiation detector is presented. The method and system are designed to dynamically control the sampling window or shaping time characteristics of a photon counting detector to accommodate variations of flux experienced by the detector so as to preserve optimum detector performance and prevent saturation during high flux conditions.

23 Claims, 3 Drawing Sheets

METHOD AND SYSTEM OF DYNAMICALLY CONTROLLING SHAPING TIME OF A PHOTON COUNTING ENERGY-SENSITIVE RADIATION DETECTOR TO ACCOMMODATE VARIATIONS IN INCIDENT RADIATION FLUX LEVELS

BACKGROUND OF THE INVENTION

The present invention relates generally to radiographic imaging and, more particularly, to a method and system of dynamically controlling shaping time of an energy-sensitive radiographic detector, such as a CT detector, to accommodate broad variations in radiation flux levels experienced by the detector. The present invention is particularly related to photon counting and/or energy discriminating radiation detectors.

Typically, in radiographic systems, an x-ray source emits x-rays toward a subject or object, such as a patient or a piece of luggage. Hereinafter, the terms "subject" and "object" may be interchangeably used to describe anything capable of being imaged. The x-ray beam, after being attenuated by the subject, impinges upon an array of radiation detectors. The intensity of the radiation beam received at the detector array is typically dependent upon the attenuation of the x-rays through the scanned object. Each detector element of the detector array produces a separate signal indicative of the attenuated beam received by each detector element. The signals are transmitted to a data processing system for analysis and further processing which ultimately produces an image.

In a similar fashion, radiation detectors are employed in emission imaging systems such as used in nuclear medicine (NM) gamma cameras and Positron Emission Tomography (PET) systems. In these systems, the source of radiation is no longer an x-ray source, rather it is a radiopharmaceutical introduced into the body being examined. In these systems each detector of the array produces a signal in relation to the localized intensity of the radiopharmaceutical concentration in the object. Similar to conventional x-ray imaging, the strength of the emission signal is also attenuated by the inter-lying body parts. Each detector element of the detector array produces a separate signal indicative of the emitted beam received by each detector element. The signals are transmitted to a data processing system for analysis and further processing which ultimately produces an image.

In most computed tomography (CT) imaging systems, the x-ray source and the detector array are rotated about a gantry encompassing an imaging volume around the subject. X-ray sources typically include x-ray tubes, which emit the x-rays as a fan or cone beam from the anode focal point. X-ray detector assemblies typically include a collimator for reducing scattered x-ray photons from reaching the detector, a scintillator adjacent to the collimator for converting x-rays to light energy, and a photodiode adjacent to the scintillator for receiving the light energy and producing electrical signals therefrom. Typically, each scintillator of a scintillator array converts x-rays to light energy. Each photodiode detects the light energy and generates a corresponding electrical signal. The outputs of the photodiodes are then transmitted to the data acquisition system and then to the processing system for image reconstruction.

Conventional CT imaging systems utilize detectors that convert x-ray photon energy into current signals that are integrated over a time period, then measured and ultimately digitized. A drawback of such detectors is their inability to provide independent data or feedback as to the energy and incident flux rate of photons detected. That is, conventional CT detectors have a scintillator component and photodiode component wherein the scintillator component illuminates upon reception of x-ray photons and the photodiode detects illumination of the scintillator component and provides an integrated electrical current signal as a function of the intensity and energy of incident x-ray photons. While it is generally recognized that CT imaging would not be a viable diagnostic imaging tool without the advancements achieved with conventional CT detector design, a drawback of these integrating detectors is their inability to provide energy discriminatory data or otherwise count the number and/or measure the energy of photons actually received by a given detector element or pixel. Accordingly, recent detector developments have included the design of an energy discriminating detector that can provide photon counting and/or energy discriminating feedback. In this regard, the detector can be caused to operate in an x-ray counting mode, an energy measurement mode of each x-ray event, or both.

These energy discriminating detectors are capable of not only x-ray counting, but also providing a measurement of the energy level of each x-ray detected. While a number of materials may be used in the construction of an energy discriminating detector, including scintillators and photodiodes, direct conversion detectors having an x-ray photoconductor, such as amorphous selenium or cadmium zinc telluride, that directly convert x-ray photons into an electric charge have been shown to be among the preferred materials. A drawback of photon counting detectors, however, is that these types of detectors have limited count rates and have difficulty covering the broad dynamic ranges encompassing very high x-ray photon flux rates typically encountered with conventional CT systems. Generally, a CT detector dynamic range of 1,000,000 to one is required to adequately handle the possible variations in photon flux rates. In the very fast scanners now available, it is not uncommon to encounter x-ray flux rates of over $10^8$ photons/$mm^2$/sec when no object is in the scan field, with the same detection system needing to count only 10's of photons that manage to traverse the center of large objects.

The very high x-ray photon flux rates ultimately lead to detector saturation. That is, these detectors typically saturate at relatively low x-ray flux levels. This saturation can occur at detector locations wherein small subject thickness is interposed between the detector and the radiographic energy source or x-ray tube. It has been shown that these saturated regions correspond to paths of low subject thickness near or outside the width of the subject projected onto the detector array. In many instances, the subject is more or less cylindrical in the effect on attenuation of the x-ray flux and subsequent incident intensity to the detector array. In this case, the saturated regions represent two disjointed regions at extremes of the detector array. In other less typical, but not rare instances, saturation occurs at other locations and in more than two disjointed regions of the detector. In the case of a cylindrical subject, the saturation at the edges of the array can be reduced by the imposition of a bowtie filter between the subject and the x-ray source. Typically, the filter is constructed to match the shape of the subject in such a way as to equalize total attenuation, filter and subject, across the detector array. The flux incident to the detector is then relatively uniform across the array and does not result in saturation. What can be problematic, however, is that the bowtie filter may not be optimum given that a subject population is significantly less than uniform and not exactly cylindrical in shape nor centrally located in the x-ray beam.

In such cases, it is possible for one or more disjointed regions of saturation to occur or conversely to over-filter the x-ray flux and unnecessarily create regions of very low flux. Low x-ray flux in the projection results in a reduction in information content which will ultimately contribute to unwanted noise in the reconstructed image of the subject.

Moreover, a system calibration method common to most CT systems involves measuring detector response with no subject whatsoever in the beam. This "air cal" reading from each detector element is used to normalize and correct the preprocessed data that is then used for CT image reconstruction. Even with ideal bowtie filters, high x-ray flux now in the central region of the detector array could lead to detector saturation during the system calibration phase.

A number of imaging techniques have been proposed to address saturation of any part of the detector. These techniques include maintenance of low x-ray flux across the width of a detector array, for example, by modulating tube current or x-ray voltage during scanning. However, this solution leads to increased scanned time. That is, there is a penalty that the acquisition time for the image is increased in proportion to the nominal flux needed to acquire a certain number of x-rays that meet image quality requirements. Other solutions include the implementation of over-range algorithms that may be used to generate replacement data for the saturated data. However, these algorithms may imperfectly replace the saturated data as well as contribute to the complexity of the CT system.

It would therefore be desirable to design an energy discriminating, photon counting CT detector that does not saturate at the x-ray photon flux rates typically found in conventional CT systems.

BRIEF DESCRIPTION OF THE INVENTION

The present invention is a directed method and apparatus for adjusting the sampling/shaping time characteristics of a radiation detector as a function of incident photon flux that overcomes the aforementioned drawbacks.

The present invention includes a method and system of counting and tagging radiating energy received by a radiation detector. The method and system are designed to dynamically control the sampling time or shaping time characteristics of a photon counting detector to accommodate large variations of flux experienced by the detector so as to prevent saturation during high flux conditions. Moreover, the present invention is designed to control the detector so as to accommodate low flux rate conditions such that detection efficiency and image quality is not sacrificed when lower flux is experienced by the detector.

A photon counting (PC) radiographic system includes a radiation energy detector configured to detect radiation energy having a given flux rate and output signals indicative of the detected radiation energy. A shaper unit with a given shaping time is connected to receive the electrical signals and conditions them to provide electrical pulses indicative of the radiation photon energy. A PC channel is connected to receive the electrical signals and sample the electrical pulse signals of a certain height or intensity indicative of the photon energy by an adjustable pulse height discriminator or threshold. The PC channel is further configured to provide a photon count output over a sampling interval. The system also includes a control operationally connected to the PC channel and configured to automatically adjust the shaping time at least as a function of the given flux rate. The system also includes a control operationally connected to the PC channel and configured to automatically adjust the sensitivity to pulse height or threshold discriminator as a function of the given flux rate or shaping time.

A CT system includes a rotatable gantry having a bore centrally disposed therein and a table movable fore and aft through the bore and configured to position a subject for CT data acquisition. A radiographic energy projection source is positioned within the rotatable gantry and configured to project radiographic energy toward the subject. The CT system further includes a detector assembly disposed within the rotatable gantry and configured to detect radiographic energy projected by the projection source and impinged by the subject. The detector assembly is defined to include detector elements configured to output electrical signals indicative of detected radiographic energy and PC channels operationally connected to the detector elements and configured to count the number of photons of the detected radiographic energy signal conditioned according to a variable shaping time. The detector elements also have shaping time controllers operationally connected to the PC channels and configured to control the variable shaping times in near real-time based on the photon output count data.

A method of preventing radiographic energy detector saturation includes monitoring flux of radiographic energy having a number of photons received by a photon counting, radiographic energy detector. The detector is designed to sample a photon charge cloud, in the case of direct conversion detectors having an x-ray photoconductor, or a photodiode current pulse, in the case of scintillator detectors, and count the number of photons using a given signal pulse shaping time. The method further includes comparing a current flux on the radiographic energy detector to a base flux level corresponding to the given shaping time and adjusting the given shaping time to correspond to the current flux based on the comparison. An additional aspect of the present invention includes automatic means for modifying the energy threshold levels so as to compensate for changing channel shaping times in order to maintain accurate photon energy information.

Therefore, in accordance with one aspect of the present invention, a single PC radiographic system includes a radiographic energy detector configured to detect radiographic energy having a given flux rate and output electrical signals indicative of the detected radiographic energy. The system further includes a PC channel connected to receive the electrical signals and sample the electrical signals in a sampling interval window and provide a photon count output. A control is operationally connected to the PC channel and configured to automatically adjust the sampling interval window at least as a function of the given flux rate.

According to another aspect, the present invention includes a CT system having a rotatable gantry having a bore centrally disposed therein, a table movable fore and aft through the bore and configured to position a subject for CT data acquisition, a radiographic energy projection source positioned within the rotatable gantry and configured to project radiographic energy toward the subject, and a detector assembly disposed within the rotatable gantry and configured to detect radiographic energy projected by the projection source and impinged by the subject. The detector assembly includes a detector element configured to output electrical signals indicative of detected radiographic energy and a PC channel operationally connected to the detector element and configured to count a number of photons of the detected radiographic energy according to a variable shaping time. The detector assembly further includes a shaping time controller operationally connected to the PC channel and configured to control the variable shaping time in near real-time based on the photon output count data.

In accordance with yet another aspect, a method of preventing radiation energy detector saturation includes monitoring flux of radiation energy having a number of photons received by a photon counting, radiation energy detector. The detector is designed to sample a photon charge cloud within a given sampling window and count the number of photons. The method further includes comparing a current flux on the radiation energy detector to a base flux level corresponding to the given sampling window and adjusting the given sampling window to correspond to the current flux based on the comparison.

Various other features, objects and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION OF THE PREFERRED EMBODIMENT

The operating environment of the present invention is described with respect to a four-slice computed tomography (CT) system. However, it will be appreciated by those skilled in the art that the present invention is equally applicable for use with single-slice or other multi-slice configurations. Moreover, the present invention will be described with respect to the detection and conversion of x-rays. However, one skilled in the art will further appreciate that the present invention is equally applicable for the detection and conversion of other radiation energy sources.

Figure 1:
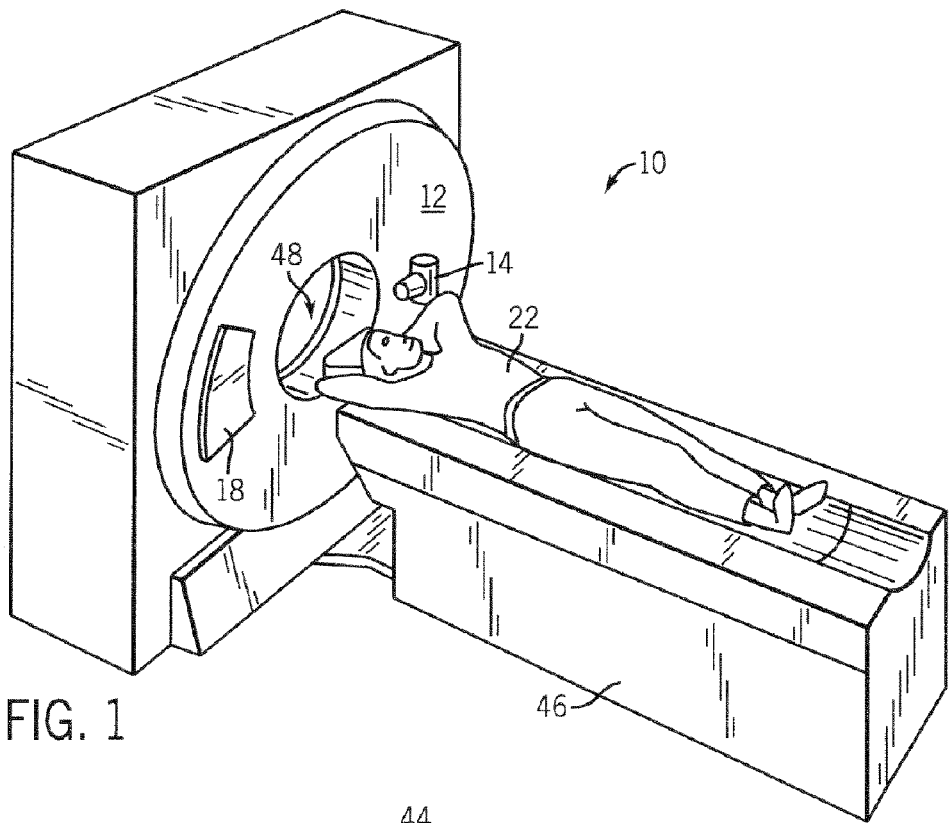
FIG. 1 is a pictorial view of a CT imaging system.
Figure 2:
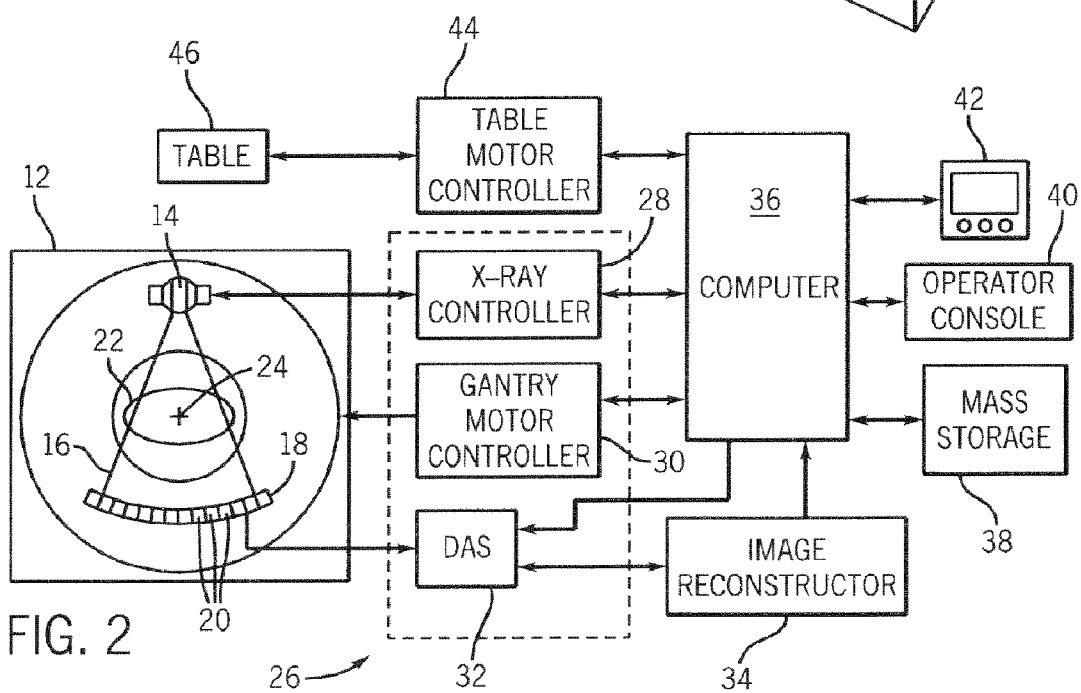
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector assembly 18 on the opposite side of the gantry 12. Detector assembly 18 is formed by a plurality of detectors 20 which together sense the projected x-rays that pass through a medical patient 22. Each detector 20 produces an electrical signal that represents not only the intensity of an impinging x-ray beam but is also capable of providing photon or x-ray count data and energy level, and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. A data acquisition system (DAS) 32 in control mechanism 26 reviews data from detectors 20 and converts the data to digital signals for subsequent processing. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has a keyboard. An associated display screen 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves portions of patient 22 through a gantry opening 48.

The present invention is directed to a radiation detector that may be incorporated with the CT system described above or other radiographic systems, such as x-ray systems or general purpose radiation detectors.

Generally, high-sensitivity photon counting radiation detectors are constructed to have a relatively low dynamic range. This is generally considered acceptable for proton counting detector applications since high flux conditions typically do not occur. In CT detector designs, low flux detector readings through the subject are typically accompanied by areas of high irradiation in air, and/or within the contours of the scan subject requiring CT detectors to have very large dynamic range responses. Moreover, the exact measurement of photons in these high-flux regions is less critical than that for low-flux areas where each photon contributes an integral part to the total collected photon statistics. Notwithstanding that the higher flux areas may be of less clinical or diagnostic value, images reconstructed with over-ranging or saturated detector channel data can be prone to artifacts. As such, the handling of high-flux conditions is also important.

The present invention includes an x-ray flux management control designed to prevent saturation of PC x-ray systems having detector channels characterized by low dynamic range. Dynamic range of a detector channel defines the range of x-ray flux levels that the detector channel can handle to provide meaningful data at the low-flux end and not experience over-ranging or saturating at the high flux end. Notwithstanding the need to prevent over-ranging, to provide diagnostically valuable data, the handling of low-flux conditions, which commonly occur during imaging through thicker cross-sections and other areas of limited x-ray transmission, is also critical in detector design. As such, the x-ray flux management control described herein is designed to satisfy both high flux and low flux conditions.

Generally, operation of a photon counting detector is characterized by a shaping time curve that is fixed. The shaping time curve defines a relationship or balance between charge integration time (single-event signal level) and detector channel recovery time so as to provide acceptable PC count-rates, noise suppression, and energy resolution. Typically, the detector channel is constructed to have a shaping time that favors low-flux rate conditions. That is, for low-flux rate conditions, which translate to fewer x-ray photons, a longer shaping time is preferred so that the entire photon charge cloud is integrated and SNR is optimized. There is generally relatively little constraint on the time necessary to integrate the entire photon cloud. Since the condition is characterized by low-flux, the detector channel is not likely to saturate while integrating or otherwise sampling the entire photon cloud. On the other hand, the low-flux rate favored, fixed time shaping may be insufficient for high-flux rate conditions. Moreover, if the time shaping is fixed to match or correspond to high-flux rate conditions, a negative impact on SNR and energy resolution during low-flux rate conditions follows.

Figure 3:
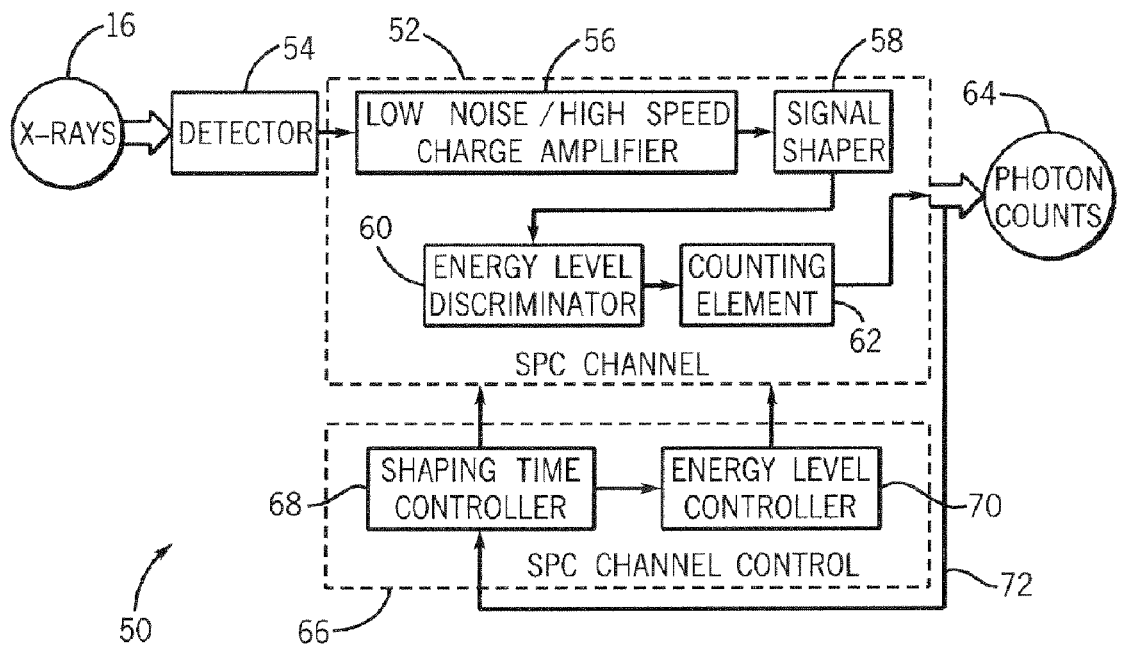
FIG. 3 is a block schematic diagram of a detector assembly according to the present invention.

Accordingly, the present invention includes a system and method to dynamically and automatically control the shaping time of a detector channel such that low-flux as well as high-flux rate conditions are optimally addressed. Referring now to FIG. 3, a block schematic diagram of an x-ray detection system 50 according to the present invention is shown. System 50 includes an PC channel 52 connected to receive electrical signals from a detector element 54. Detector 54 is constructed to detect x-rays 16 projected by an x-ray source and attenuated by a subject, such as a medical patient. It is understood that the present invention is applicable with gamma rays and other forms of radiographic energy.

PC channel 52 includes a low-noise/high-speed charge amplifier 56 connected to receive the electrical signals from detector element 54. The amplified output of amplifier 56 is then input to a signal shaper 58 constructed to extract individual photon events from the electrical signals. Energy level discriminator 60 is connected to signal shaper 58 and is designed to filter photons based on their pulse height energy level relative to one or more thresholds. To this end, those photons having energy levels outside a desired range are excluded from counting and processing for image reconstruction. Minimally, discriminator 60 is designed to exclude those photons having an energy level corresponding to noise in the system. It is contemplated that multiple thresholds may be used to define energy level ranges. Counting element 62 receives those photons not filtered out by energy level discriminator 60 and is constructed to count the number of photons received at the detector and provide a corresponding output 64. As will be described and in contrast to known PC channels, operation PC channel 52 is governed by a variable shaping time.

PC channel 52 is operationally connected to a control 66 that includes a shaping time controller 68 and, preferably, an energy level controller 70. While it is preferred that control 66 include energy level controller 70, it is contemplated that the present invention may be carried out without it. In one embodiment, PC channel 52 includes an active filter whose operation defines the channel's shaping time. In this regard, resistive and capacitive characteristics of the active filter can be adjusted to manipulate the channel's shaping time properties.

Shaping time controller 68 is connected to PC channel 52 and is designed to adjust the shaping time characteristics of PC channel 52 based on photon count feedback received across feedback loop 72. More particularly, shaping time controller 68 increases the channel's shaping time when the detector element is exposed to low x-ray flux as measured by the number of photons counted 64. In contrast, when the x-ray flux on the detector element 54 increases, the time shaping controller decreases the time shaping or sampling window of PC channel 52.

As such, when the detector is experiencing higher x-ray flux, the amount of time the PC channel spends sampling the photon charge cloud is reduced. Accordingly, less precise photon and energy discriminatory data with respect to the photon charge cloud is determined; however, the channel recovers at a rate sufficient to avoid over-ranging. In this regard, as the shaping time or sampling window is caused to decrease, more photons are inspected for data, i.e. counted, while each detected photon provides less precise energy discriminatory information. And, under high flux conditions, each individual photon assumes less importance and the overall system performance and image quality is minimally impacted by the reduced SNR. On the other hand, when the detector is experiencing lower x-ray flux, the amount of time the PC channel spends to sample the photon charge cloud is lengthened which allows sufficient time to sample the entire photon charge cloud and attain relatively precise photon count and energy discriminatory data.

As referenced above, control 66 includes, in one embodiment, an energy level controller 70. Since the measured photon signal levels vary with channel shaping time, automatic energy discriminator energy level controller 70 is coupled to shaping time controller 68 and PC channel 52 to adjust or otherwise calibrate the energy level threshold of the PC channel in response to an adjustment in the shaping time. By performing appropriate channel calibration, photons having an acceptable or decreased energy level are counted to assure linear energy response independent of channel shaping time and count rate.

Figure 4:
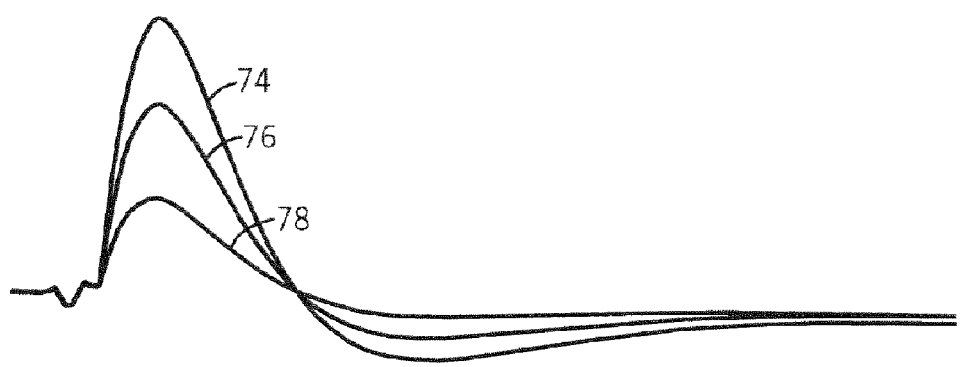
FIG. 4 is a graph illustrating signal amplitude plots for a number of shaping times for an exemplary PC detector.

Referring now to FIG. 4, a number of amplitude plots for several shaping time curves for an exemplary PC channel are illustrated. Decreasing the shaping time increases the potential count rate but, as shown, decreases the signal amplitude and increases noise. Specifically, adjusting the time shaping defined by curve 74 to that defined by curve 76 increases the potential count rate, but causes an inversely related decline in collective signal strength of the counted photons and negatively affects SNR. A further decrease in shaping time, i.e. curve 76 to curve 78 results in a further increase in count rate potential, but with additional decline in signal strength and SNR.

Figure 5:
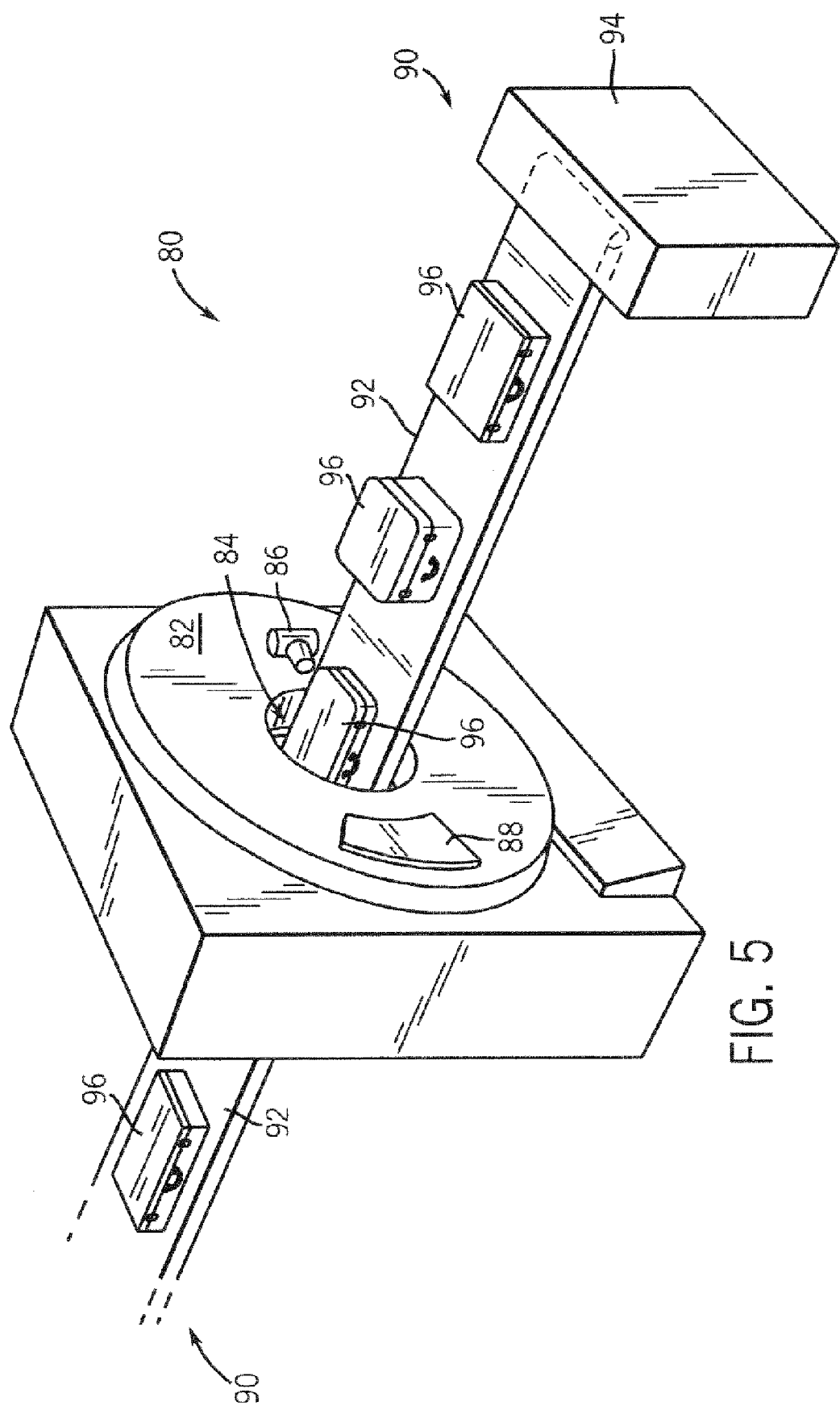
FIG. 5 is a pictorial view of a CT system for use with a non-invasive package inspection system.

Referring now to FIG. 5, package/baggage inspection system 80 includes a rotatable gantry 82 having an opening 84 therein through which packages or pieces of baggage may pass. The rotatable gantry 82 houses a high frequency electromagnetic energy source 86 as well as a detector assembly 88. A conveyor system 90 is also provided and includes a conveyor belt 92 supported by structure 94 to automatically and continuously pass packages or baggage pieces 96 through opening 84 to be scanned. Objects 96 are fed through opening 84 by conveyor belt 92, imaging data is then acquired, and the conveyor belt 92 removes the packages 96 from opening 84 in a controlled and continuous manner. As a result, postal inspectors, baggage handlers, and other security personnel may non-invasively inspect the contents of packages 96 for explosives, knives, guns, contraband, etc.

Therefore, the present invention includes a PC radiographic system. The radiographic system includes a radiographic energy detector configured to detect radiographic energy having a given flux rate and output electrical signals indicative of the detected radiographic energy. A PC channel is connected to receive the electrical signals and sample the electrical signals in a sampling interval. The PC channel is further configured to provide a photon count output. The system also includes a control operationally connected to the PC channel and configured to automatically adjust the sampling interval at least as a function of the given flux rate.

A CT system is presented and includes a rotatable gantry having a bore centrally disposed therein and a table movable fore and aft through the bore and configured to position a subject for CT data acquisition. A radiographic energy projection source is positioned within the rotatable gantry and configured to project radiographic energy toward the subject. The CT system further includes a detector assembly disposed within the rotatable gantry and configured to detect radiographic energy projected by the projection source and impinged by the subject. The detector assembly is defined to include detector elements configured to output electrical signals indicative of detected radiographic energy and PC channels operationally connected to the detector elements and configured to count the number of photons of the detected radiographic energy according to a variable shaping time. The detector assembly also have shaping time controllers operationally connected to the PC channels and configured to control the variable shaping times in near real-time based on the photon output count data.

The present invention further includes a method of preventing radiation detector saturation. The method includes monitoring flux of radiation energy having a number of photons received by a photon counting, radiation energy detector. The detector is designed to sample a photon charge cloud within a given sampling window and count the number of photons. The method further includes comparing a current flux on the radiation energy detector to a base flux level corresponding to the given sampling window and adjusting the given sampling window to correspond to the current flux based on the comparison.

The present invention has been described in terms of the preferred embodiment, and it is recognized that equivalents, alternatives, and modifications, aside from those expressly stated, are possible and within the scope of the appending claims.

What is claimed is:

1. A photon counting (PC) radiographic system comprising:
    a radiographic energy detector configured to detect radiographic energy passing through an object to be imaged and having a given flux rate and output electrical signals indicative of the detected radiographic energy;
    a PC channel connected to receive the electrical signals and sample the electrical signals in a sampling window and provide a photon count output; and
    a control operationally connected to the PC channel and configured to automatically adjust the sampling window at least as a function of the given flux rate.

2. The system of claim 1 wherein the control is further configured to decrease the sampling window with an increase in the given flux rate.

3. The system of claim 1 wherein the control is further configured to increase the sampling window with a decrease in the given flux rate.

4. The system of claim 1 further comprising a feedback loop between the photon count output and the control, and wherein the control is further configured to determine the given flux rate based on photon count data received across the feedback loop.

5. The system of claim 1 wherein the control is further configured to adjust an energy level threshold based on an adjustment of the sampling window to accept photons with acceptable energy levels.

6. The system of claim 1 wherein the radiographic energy detector is configured to detect radiation energy with a wavelength less than 10 nanometers.

7. The system of claim 6 wherein the radiation energy detector is configured to detect x-ray energy.

8. A CT system comprising:
    a rotatable gantry having a bore centrally disposed therein;
    a table movable fore and aft through the bore and configured to position a subject to be imaged for CT data acquisition;
    a radiographic energy projection source positioned within the rotatable gantry and configured to project radiographic energy toward the subject; and
    a detector assembly disposed within the rotatable gantry and configured to detect radiographic energy projected by the projection source and impinged by the subject, the detector assembly including:
        a detector element configured to output electrical signals indicative of detected radiographic energy attenuated by the subject;
        a PC channel operationally connected to the detector element and configured to count a number of photons of the detected radiographic energy according to a variable shaping time; and
        a shaping time controller operationally connected to the PC channel and configured to control the variable shaping time in near real-time based on the photon output count data.

9. The CT system of claim 8 wherein the radiographic energy includes x-ray energy, and wherein the table is designed to position a medical patient within the bore.

10. The CT system of claim 8 wherein the shaping time controller is further configured to shorten the variable shaping time as the number of photons counted increases.

11. The CT system of claim 8 wherein the shaping time controller is further configured to lengthen the variable shaping time as the number of photons counted decreases.

12. The CT system of claim 8 wherein the number of photons counted is a function of flux of the radiographic energy received by the detector element.

13. The CT system of claim 8 wherein the shaping time controller is further configured to control the variable shaping time to prevent saturation of the PC channel.

14. The CT system of claim 13 wherein the variable shaping time defines a balance between charge integration time and channel recovery time.

15. The CT system of claim 8 wherein the PC channel includes:
    a low-noise, high-speed charge amplifier;
    a signal shaper operationally connected to the low-noise, high-speed charge amplifier designed to extract individual photon events;
    an energy level discriminator operationally connected to the signal shaper and designed to identify a photon energy for each photon event; and
    a photon counting element operationally connected to the energy level discriminator and designed to count the number of photons for a number of photon identified energies.

16. The CT system of claim 8 further comprising an energy level controller operationally connected to the shaping time controller and designed to accept photon events for counting having acceptable energy levels.

17. The CT system of claim 16 wherein the energy level controller is further designed to assure linear energy response independent of the variable shaping time and/or the number of photons counted.

18. A method of preventing radiation energy detector saturation comprising the steps of:
    monitoring flux of radiation energy that has passed through an object to be imaged, the radiation energy having a number of photons received by a photon counting, radiation energy detector, the detector designed to sample a photon charge cloud within a given sampling window and count the number of photons;

comparing a current flux on the radiation energy detector to a base flux level corresponding to the given sampling window; and adjusting the given sampling window to correspond to the current flux based on the comparison.

19. The method of claim 18 wherein the step of adjusting includes the step of lengthening the given sampling window if a level of the current flux is less than the base flux.

20. The method of claim 18 wherein the step of adjusting includes the step of shortening the given sampling window if a level of the current flux is more than the base flux.

21. The method of claim 18 wherein the step of monitoring includes the step of receiving an indication of the number of photons counted by the radiation detector.

22. The method of claim 18 further comprising the step of automatically adjusting an energy level threshold in response to an adjustment of the given sampling window.

23. The method of claim 18 further comprising the step of data processing and reconstructing an image of a subject and wherein the image includes tissue differentiation.

* * * * *